United States Patent
Romero et al.

(10) Patent No.: US 12,312,299 B2
(45) Date of Patent: May 27, 2025

(54) SYSTEMS AND METHODS FOR PURIFYING SOLVENTS

(71) Applicant: Fujifilm Electronic Materials U.S.A., Inc., N. Kingstown, RI (US)

(72) Inventors: Eduardo Ramirez Romero, Grapevine, TX (US); David Bollinger, Grapevine, TX (US)

(73) Assignee: Fujifilm Electronic Materials U.S.A., Inc., N. Kingstown, RI (US)

( * ) Notice: Subject to any disclaimer, the term of this patent is extended or adjusted under 35 U.S.C. 154(b) by 0 days.

(21) Appl. No.: 17/213,325

(22) Filed: Mar. 26, 2021

(65) Prior Publication Data

US 2021/0300850 A1    Sep. 30, 2021

Related U.S. Application Data

(60) Provisional application No. 63/000,747, filed on Mar. 27, 2020.

(51) Int. Cl.
| | |
|---|---|
| *C07C 29/76* | (2006.01) |
| *B01D 15/08* | (2006.01) |
| *B01D 71/26* | (2006.01) |
| *B01D 71/36* | (2006.01) |

(52) U.S. Cl.
CPC ............ *C07C 29/76* (2013.01); *B01D 15/08* (2013.01); *B01D 71/261* (2022.08); *B01D 71/262* (2022.08); *B01D 71/36* (2013.01); *B01D 2257/80* (2013.01); *B01D 2311/2512* (2022.08); *B01D 2311/2623* (2013.01)

(58) Field of Classification Search
CPC ........ C07C 29/76; B01D 15/08; B01D 71/26; B01D 71/36; B01D 2257/80; B01D 2311/2623
See application file for complete search history.

(56) References Cited

U.S. PATENT DOCUMENTS

| | | | | |
|---|---|---|---|---|
| 4,105,679 | A * | 8/1978 | Tanabe | C07D 307/08 549/507 |
| 4,188,499 | A | 2/1980 | Walter et al. | |
| 6,179,132 | B1 * | 1/2001 | Moya | C08J 5/2293 427/244 |
| 6,733,637 | B1 * | 5/2004 | Burton | C07C 29/80 203/99 |
| 9,339,766 | B2 * | 5/2016 | Takahashi | B01D 61/58 |
| 2006/0185688 | A1 | 8/2006 | Uematsu | |
| 2007/0131611 | A1 | 6/2007 | Peng et al. | |

(Continued)

FOREIGN PATENT DOCUMENTS

| | | |
|---|---|---|
| CN | 1887842 A | 1/2007 |
| CN | 105555747 | 5/2016 |

(Continued)

OTHER PUBLICATIONS

Chemeurope, "Nafion", Aug. 2011 (Year: 2011).*

(Continued)

*Primary Examiner* — Chester T Barry
(74) *Attorney, Agent, or Firm* — Fish & Richardson P.C.

(57) ABSTRACT

The present disclosure is directed to methods and systems of purifying solvents. The purified solvents can be used for cleaning a semiconductor substrate in a multistep semiconductor manufacturing process.

25 Claims, 1 Drawing Sheet

(56) References Cited

U.S. PATENT DOCUMENTS

| | | | |
|---|---|---|---|
| 2011/0004031 A1 | 1/2011 | Cruz et al. | |
| 2014/0163264 A1* | 6/2014 | Takahashi | B01D 61/362 210/180 |
| 2014/0216446 A1 | 8/2014 | Wruck | |
| 2015/0144557 A1* | 5/2015 | Ly | B01D 15/00 210/260 |
| 2016/0200649 A1 | 7/2016 | Park et al. | |
| 2017/0005321 A1 | 1/2017 | Sugata | |
| 2019/0062159 A1* | 2/2019 | Kamimura | C11D 7/04 |
| 2019/0219924 A1 | 7/2019 | Kamimura | |
| 2019/0352244 A1 | 11/2019 | Yamamura et al. | |
| 2021/0061741 A1* | 3/2021 | Kim | C07C 31/10 |
| 2021/0220754 A1* | 7/2021 | Ahmadiannamini | B01D 15/362 |
| 2021/0300851 A1 | 9/2021 | Romero et al. | |
| 2022/0234037 A1* | 7/2022 | Takada | B01J 47/026 |
| 2023/0257331 A1 | 8/2023 | Romero et al. | |

FOREIGN PATENT DOCUMENTS

| | | | | |
|---|---|---|---|---|
| CN | 106132516 | | 11/2016 | |
| CN | 107365246 | | 11/2017 | |
| CN | 108707509 A | | 10/2018 | |
| JP | 1994100616 | * | 4/1994 | C08F 6/24 |
| JP | H11-506431 A | * | 6/1999 | |
| JP | H 11310649 | | 11/1999 | |
| JP | 2003-112060 | | 4/2003 | |
| JP | 2003-251120 A | | 9/2003 | |
| JP | 2004016526 A | * | 1/2004 | |
| JP | 4801870 B2 | * | 10/2011 | C07C 29/80 |
| JP | 2013-23440 | | 2/2013 | |
| JP | 2013-023440 A | | 2/2013 | |
| JP | 2013-023442 A | | 2/2013 | |
| JP | 5930921 | | 6/2016 | |
| TW | 201921175 | | 6/2019 | |
| WO | WO-0114595 A2 | * | 3/2001 | C13B 10/00 |
| WO | WO-2010117845 A | * | 10/2010 | B01D 65/10 |
| WO | WO-2018043697 A1 | * | 3/2018 | B01D 15/00 |
| WO | WO 2018051716 | | 3/2018 | |
| WO | WO 2019181387 | | 9/2019 | |
| WO | WO 2019191520 A1 | | 10/2019 | |

OTHER PUBLICATIONS

WIPO Translation of JP1994100616 (Year: 1994).*

Umeda et al, "Metal Reduction at Point-of-use Filtration", Advances in Patterning Materials and Processes XXXIII, 2016, pp. 1-7 (Year: 2016).*

Headline, "PTFE Housings", Jul. 2017, pp. 1-4 (Year: 2017).*

Gunze, "What is Fluorine Resin", Jun. 2015, pp. 1-3 (Year: 2015).*

Espacenet Translation of WO2018043697A1 Kamimura, (Year: 2018).*

Umeda et al, "Metal Reduction at Bulk Chemical Filtration", Advances in Patterning Materials and Processes XXXIII, 2016, pp. 1-9 (Year: 2017).*

Takahira, Ruthenium-Catalyzed Olefin Cross-Metathesis with Tetrafluoroethylene and Analogous Fluoroolefins, J. Am. Chem. Soc. 2015, 137, 7031-7034 (Year: 2015).*

Machine translation of Koizumi, JP2003112060 A (Year: 2003).*

International Search Report and Written Opinion for the International Searching Authority for International Application No. PCT/US2021/024282, dated Jun. 8, 2021.

Wikipedia "Ion Exchange", retrieved from https://en.wikipedia.org/w/index.php?=Ion_exchange&oldid=874816544, (Dec. 21, 2018).

Wikipedia Molecular Sieve, retrieved from https://en.wikipedia.org/w/index.php?title=Molecular_sieve&id=879062125, (Jan. 18, 2019).

International Search Report and Written Opinion of the International Searching Authority for International Application No. PCT/US2021/024284, dated Jun. 9, 2021.

Wikipedia, "Glycerol", retrieved from https://en.wikipedia.org/w/index.php?title=Glycerol&oldid=935198612, dated Jan. 11, 2020.

Lewatit "Product Information Lewatit MonoPlus S 100", retrieved from https://www.lenntech.com/Data-sheets/Lewatit-MonoPlus-MP-64-L.pdf, dated Oct. 19, 2005.

US Energy Information Administration "Vacuum distillation is a key part of the petroleum refining process", retrieved from https://www.eia.gov/todayinenergy/detail.php?id=9130#:-:text=As%20the%20name%20vacuum%20distillation.%2C%20or%20degrading%2C%20the%20oil, dated Dec. 10, 2012.

Jacquemart et al., "Membrane adsorbers, columns: single-use alternatives to resin chromatography," BioProcess International, Jan. 20, 2017, 4 pages.

Office Action in Taiwan Appln. No. 110110863, dated Aug. 16, 2024, 5 pages (with English translation).

Extended European Search Report in European Appln No. 21776392.9, dated Jul. 20, 2023, 10 pages.

Extended European Search Report in European Appln No. 21776393.7, dated Jul. 25, 2023, 10 pages.

IonKleen, "SL Purifier: Microlithography Purifier Data Sheet 574a," 2004, 2 pages.

Office Action in Japanese Appln. No. 2022-559290, dated Feb. 26, 2025, 9 pages (with English translation).

Office Action in Chinese Appln. No. 202180038276.7, dated Apr. 21, 2025, 18 pages (with English translation).

\* cited by examiner

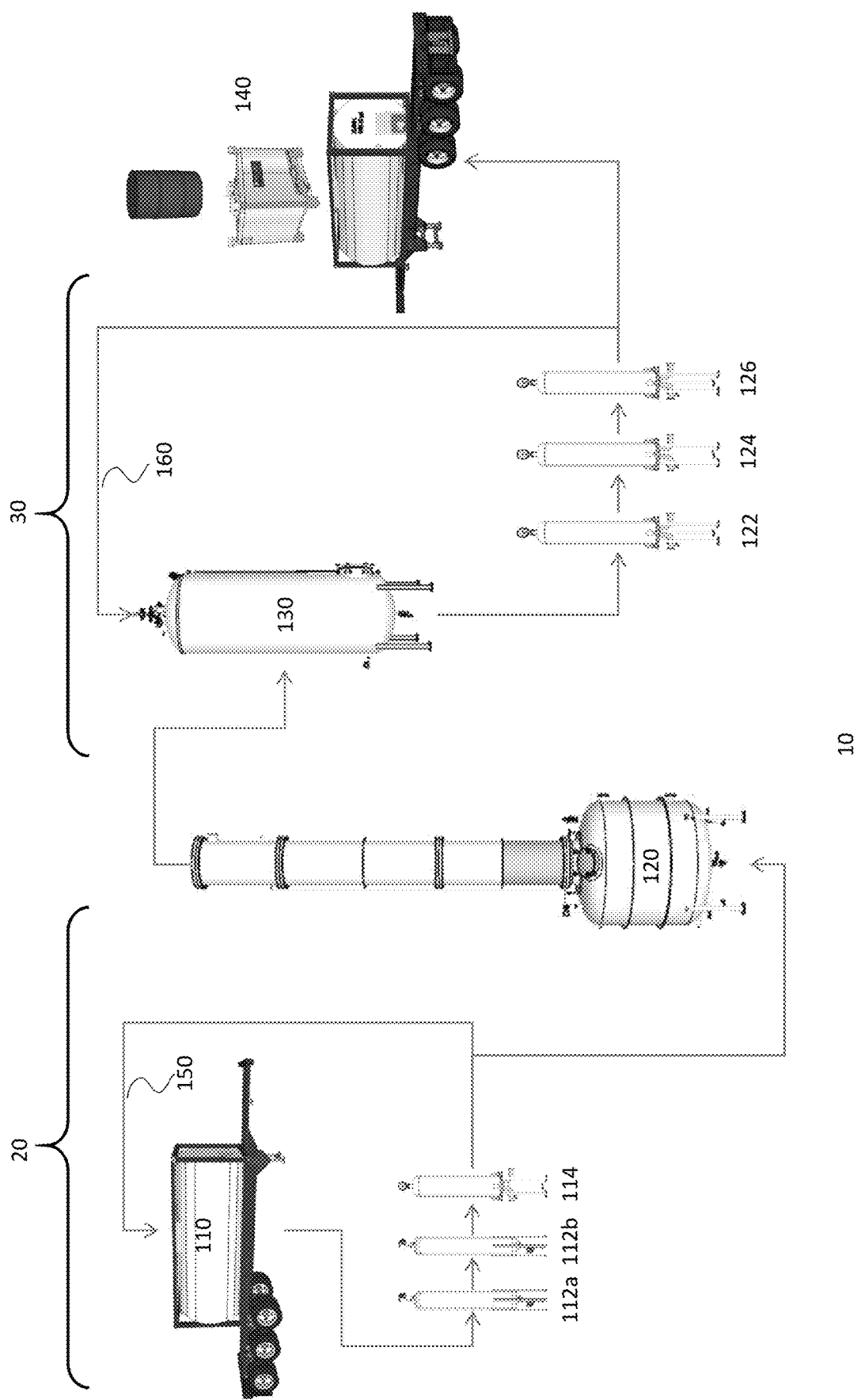

SYSTEMS AND METHODS FOR PURIFYING SOLVENTS

CROSS-REFERENCE TO RELATED APPLICATION

The present application claims priority to U.S. Provisional Application Ser. No. 63/000,747, filed on Mar. 27, 2020, the contents of which are hereby incorporated by reference in their entirety.

FIELD OF THE DISCLOSURE

The present disclosure relates to systems and methods for purifying solvents (e.g., organic solvents). In particular, the present disclosure relates to systems and methods that can be used to obtain organic solvents having a very low amount of organic and metal impurities.

BACKGROUND OF THE DISCLOSURE

The semiconductor industry has achieved rapid improvements in integration density of electronic components, which are arisen from continuous reductions in the component size. Ultimately, more of the smaller components are afforded to be integrated into a given area. These improvements are mostly due to the development of new precision and high resolution processing techniques.

During the manufacturing of high resolution integrated circuits (ICs), various processing liquids will come into contact with a bare wafer or a film-coated wafer. For example, the fabrication of a fine metal interconnection typically involves a procedure of coating a base material with a pre-wetting liquid before the base material is coated with a composite liquid to form a resist film. These processing liquids, containing proprietary ingredients and various additives, are known to be a source of contamination of IC wafer.

It is believed that even if a trace amount of contaminants is mixed into these chemical liquids, such as a wafer pre-wetting liquid or a developer solution, the resulting circuit patterns may have defects. For example, it is known that the presence of very low levels of metal impurities may interfere with the performance and stability of semiconductor devices. Depending on the kind of metallic contaminants, oxide property can deteriorate, inaccurate patterns can be formed, electrical performance of semiconductor circuits can be impaired, which eventually adversely impact manufacturing yields.

The contamination of impurities, such as metal impurities, fine particles, organic impurities, moisture, and the like, can be inadvertently introduced in a chemical liquid during various stages of the manufacturing of the chemical liquid. Examples include impurities that are presented in a raw material, a by-product generated or an unreacted reactant remained when the chemical liquid is manufactured, or foreign matters eluded or extracted from the surface of the manufacturing apparatus or from a container equipment, reaction vessels, or the like used in transporting, storing or reacting. Hence, a reduction or removal of insoluble and soluble contaminants from these chemical liquids used for the production of highly precise and ultra-fine semiconductor electronic circuits is a basic assurance of producing defective-free ICs.

In this respect, it is imperative to significantly improve and to rigorously control the standard and quality of chemical liquid manufacturing processes and systems in order to form high purity chemical liquids, which are indispensable in the fabrication of ultra-fine and immensely precise semiconductor electronic circuits.

SUMMARY OF THE DISCLOSURE

Accordingly, to form highly precise integrated circuits, the demands for ultra-pure chemical liquids, and the quality improvement and control of theses liquids become very critical. Specific key parameters targeted for quality improvement and control include: liquid and on-wafer metal reduction, liquid and on-wafer particle count reduction, on-wafer defect reduction, and organic contaminant reduction.

In view of the above, the present disclosure provides a purification system and a method of purifying a solvent (e.g., an organic solvent) using the same for preparing a solvent targeted for semiconductor manufacturing, in which an ultra-pure solvent is produced with the amounts of metallic impurities, organic impurities, and residual moisture in the solvent managed within predetermined ranges and without the generation or introduction of unknown and unwanted substances. Hence, the occurrence of residue and/or particle defects is suppressed and the yield of semiconductor wafer is improved. In addition, the inventors found unexpectedly that purifying an organic solvent using both dehydration (e.g., by using a molecular sieve column) and filtration (e.g., by using a filter having a certain pore size) before solvent distillation can result in a purified organic solvent having a very low amount of organic impurities (e.g., at least about 99.99%) and/or a very low moisture content (e.g., at most about 100 ppm). Further, the inventors found unexpectedly that purifying an organic solvent using two different types of negatively charged ion exchange filters (e.g., one capable of removing heavy metals such as Fe, Ni, Cr, Zn, or Cu and one capable of removing alkali or alkaline earth metals such as K, Na, or Ca) after solvent distillation can result in a purified organic solvent having a surprisingly low total amount of metal impurities (e.g., at most about 200 ppt).

In one aspect, the disclosure features a method of purifying an organic solvent that includes (1) passing the organic solvent through at least one column containing an adsorbent to remove water in the organic solvent, (2) passing the organic solvent through a first filter unit, in which the first filter unit includes a first housing and at least one first filter in the first housing, and the at least one first filter includes a filtration medium; and (3) distilling the organic solvent in a distillation column to obtain a purified organic solvent. The first filter unit is between the distillation column and the at least one column containing the adsorbent.

In another aspect, the disclosure features a system that includes (1) at least one column containing an adsorbent, (2) a first filter unit downstream of and in fluid communication with the at least one column containing an adsorbent, in which the first filter unit includes a first housing and at least one first filter in the first housing, and the first filter includes a filtration medium; and (3) a distillation column downstream of and in fluid communication with the first filter unit.

In another aspect, the disclosure features a method of purifying an organic solvent that includes (1) distilling the organic solvent in a distillation column to obtain a distilled organic solvent; and (2) passing the distilled organic solvent through an ion exchange filter unit to obtain a purified organic solvent. The ion exchange filter unit includes a housing and at least one first ion exchange filter and at least one second ion exchange filter in the housing. The at least one first ion exchange filter and the at least one second ion exchange filter are both negatively charged ion exchange filters and are connected in series. The at least one first ion exchange filter is different from the at least one second ion exchange filter.

In another aspect, the disclosure features a system that includes (1) a distillation column; and (2) an ion exchange filter unit downstream of and in fluid communication with the distillation column. The ion exchange filter unit includes a housing and at least one first ion exchange filter and at least one second ion exchange filter in the housing. The at least one first ion exchange filter and the at least one second ion exchange filter are both negatively charged ion exchange filters and are connected in series. The at least first ion exchange filter is different from the at least one second ion exchange filter.

Embodiments can include on or more of the following features.

In some embodiments, the organic solvent includes an alcohol (e.g., isopropyl alcohol).

In some embodiments, the adsorbent includes a molecular sieve, a silica gel, activated alumina, activated carbon or an ion exchange resin.

In some embodiments, the filtration medium in the at least one first filter includes a polyolefin (e.g., high density polyethylene or polytetrafluoroethylene), a polyamide, a fluoropolymer, or a copolymer thereof.

In some embodiments, the filtration medium in the at least one first filter has an average pore size from about 0.1 μm to 0.25 μm.

In some embodiments, the first filter unit includes two to five first filters. In some embodiments, the first filters are connected in parallel. In some embodiments, the at least one first filter is a particle removal filter.

In some embodiments, the method further includes recirculating the organic solvent before distilling the organic solvent in the distillation column. In some embodiments, the recirculating includes moving the organic solvent exiting the first filter unit to the at least one column containing an adsorbent and subsequently passing the organic solvent through the at least one column containing an adsorbent and the first filter unit.

In some embodiments, the method further includes passing the organic solvent through a second filter unit downstream of the distillation column, in which the second filter unit includes a second housing and at least one second filter in the second housing, and the at least one second filter includes a filtration medium.

In some embodiments, the at least one first or second ion exchange filter includes a filtration medium that includes a polyolefin, a polyamide, a fluoropolymer, or a copolymer thereof. In some embodiments, the filtration medium in the at least one first or second ion exchange filter includes a polyethylene having sulfonate groups or a polytetrafluoroethylene having sulfonate groups, or a copolymer thereof.

In some embodiments, the ion exchange filter unit (e.g., third filter unit 124 shown in FIG. 1) includes two to five first ion exchange filters. In some embodiments, the first ion exchange filters are connected in parallel. In some embodiments, the at least one first ion exchange filter is capable of removing at least 90 wt % of Fe, Ni, Cr, Zn, and/or Cu from the organic solvent.

In some embodiments, the ion exchange filter unit (e.g., third filter unit 124 shown in FIG. 1) includes two to five second ion exchange filters. In some embodiments, the second ion exchange filters are connected in parallel. In some embodiments, the at least one second ion exchange filter is capable of removing at least 70 wt % of K, Na, and/or Ca from the organic solvent.

In some embodiments, the method further includes passing the organic solvent through a filter unit (e.g., second filter unit 122 shown in FIG. 1) in fluid communication with and between the distillation column and the ion exchange filter unit (e.g., third filter unit 124 shown in FIG. 1). In some embodiments, the filter unit between the distillation column and the ion exchange filter unit includes a housing and at least one particle removal filter in the housing. In some embodiments, the at least one particle removal filter includes a filtration medium that includes a polyolefin, a polyamide, a fluoropolymer (e.g., a polytetrafluoroethylene), or a copolymer thereof. In some embodiments, the at least one particle removal filter includes a filtration medium having an average pore size of from about 5 nm to about 50 nm.

In some embodiments, the method further includes passing the organic solvent through a filter unit (e.g., fourth filter unit 126 shown in FIG. 1) downstream of and in fluid communication with the ion exchange filter unit (e.g., third filter unit 124 shown in FIG. 1). In some embodiments, the filter unit downstream of the ion exchange filter unit includes a housing and at least one particle removal filter in the housing. In some embodiments, the at least one particle removal filter in the filter unit downstream of the ion exchange filter unit includes a filtration medium that includes a polyolefin, a polyamide, a fluoropolymer (e.g., a polytetrafluoroethylene), or a copolymer thereof. In some embodiments, the at least one particle removal filter in the filter unit downstream of the ion exchange filter unit includes a filtration medium having an average pore size of from about 2 nm to about 10 nm.

In some embodiments, the method further includes recirculating the organic solvent exiting the filter unit downstream of the ion exchange filter unit. In some embodiments, the recirculating includes moving the organic solvent exiting the filter unit downstream of the ion exchange filter unit to a storage tank and subsequently passing the organic solvent from the storage tank through the ion exchange filter unit.

In some embodiments, the method further includes moving the purified solvent to a packaging station.

In some embodiments, the purified organic solvent has a purity of at least about 99.99%. In some embodiments, the purified organic solvent has a moisture content of at most about 100 ppm. In some embodiments, the purified organic solvent includes metal impurities in a total amount of at most about 200 ppt of the purified organic solvent.

BRIEF DESCRIPTION OF THE DRAWING

FIG. 1 is a schematic diagram showing an example of a purification system adopted in a method of purifying an organic solvent in accordance with some embodiments of the present disclosure.

DETAILED DESCRIPTION OF THE DISCLOSURE

As defined herein, unless otherwise noted, all percentages expressed should be understood to be percentages by weight to the total weight of a composition. Unless otherwise noted, ambient temperature is defined to be between about 16 and about 27 degrees Celsius (° C.). The term "solvent" mentioned herein, unless otherwise noted, refers to a single solvent or a combination of two or more (e.g., three or four) solvents. In the present disclosure, "ppm" means "parts-permillion", "ppb" means "parts-per-billion" and "ppt" means "parts-per-trillion", based on the total weight of a composition.

In general, the disclosure features systems and methods for purifying a solvent (e.g., an organic solvent). The solvent mentioned herein can be used in a wafer processing solution (such as a pre-wetting liquid, a developer solution, a rinsing solution, a cleaning solution, or a stripping solution), or a solvent for a semiconductor material used in any semiconductor manufacturing process.

Prior to being subjected to a purification method of the present disclosure, a solvent may contain an undesirable amount of contaminants and impurities (such as organic impurities, metal impurities, and moisture). After the solvent is processed by the purification method of the present disclosure, substantial amounts of the contaminants and impurities can be removed from the solvent. A pre-processed solvent is also referred to herein as an "unpurified solvent". The pre-processed solvent can be synthesized in house or commercially available via purchasing from a supplier. A post-processed solvent is also referred to herein as a "purified solvent". A "purified solvent" can include impurities limited within predetermined ranges.

In general, the solvent mentioned herein can include at least one (e.g., two, three, or four) organic solvent, such as an alcohol, an ether, a hydrocarbon, a halogenated hydrocarbon, an ester, a ketone, or a carbonate. Examples of suitable organic solvents include methanol, ethanol, 1-propanol, isopropanol, n-propanol, 2-methyl-1-propanol, n-butanol, 2-butanol, tert-butanol, 1-pentanol, 2-pentanol, 3-pentanol, n-hexanol, cyclohexanol, 2-methyl-2-butanol, 3-methyl-2-butanol, 2-methyl-1-butanol, 3-methyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 2-ethyl-1-butanol, 2,2-dimethyl-3-pentanol, 2,3-dimethyl-3-pentanol, 2,4-dimethyl-3-pentanol, 4,4-dimethyl-2-pentanol, 3-ethyl-3-heptanol, 1-heptanol, 2-heptanol, 3-heptanol, 2-methyl-2-hexanol, 2-methyl-3-hexanol, 5-methyl-1-hexanol, 5-methyl-2-hexanol, 2-ethyl-1-hexanol, methylcyclohexanol, trimethylcyclohexanol, 4-methyl-3-heptanol, 6-methyl-2-heptanol, 1-octanol, 2-octanol, 3-octanol, 2-propyl-1-pentanol, 2,6-dimethyl-4-heptanol, 2-nonanol, 3,7-dimethyl-3-octanol, ethylene glycol, propylene glycol, diethyl ether, dipropyl ether, diisopropyl ether, butyl methyl ether, butyl ethyl ether, butyl propyl ether, dibutyl ether, diisobutyl ether, tert-butyl methyl ether, tert-butyl ethyl ether, tert-butyl propyl ether, di-tert-butyl ether, dipentyl ether, diisoamyl ether, cyclopentyl methyl ether, cyclohexyl methyl ether, bromomethyl methyl ether, α,α-dichloromethyl methyl ether, chloromethyl ethyl ether, 2-chloroethyl methyl ether, 2-bromoethyl methyl ether, 2,2-dichloroethyl methyl ether, 2-chloroethyl ethyl ether, 2-bromoethyl ethyl ether, (+)-1,2-dichloroethyl ethyl ether, 2,2,2-trifluoroethyl ether, ethyl vinyl ether, butyl vinyl ether, allyl ethyl ether, allyl propyl ether, allyl butyl ether, diallyl ether, 2-methoxypropene, ethyl-1-propenyl ether, cis-1-bromo-2-ethoxyethylene, 2-chloroethyl vinyl ether, allyl-1,1,2,2-tetrafluoroethyl ether, octane, isooctane, nonane, decane, methylcyclohexane, decalin, xylene, ethylbenzene, diethylbenzene, cumene, sec-butylbenzene, cymene, dipentene, methyl pyruvate, monomethyl ether, propylene glycol monomethyl ether, propylene glycol monoethyl ether, propylene glycol monopropyl ether, propylene glycol monomethyl ether acetate, ethyl lactate, methyl methoxypropionate, cyclopentanone, cyclohexanone, n-butyl acetate, γ-butyrolactone, diisoamyl ether, isoamyl acetate, chloroform, dichloromethane, 1,4-dioxane, hexyl alcohol, 2-heptanone, isoamyl acetate, propylene carbonate, and tetrahydrofuran.

In some embodiments, the solvent is a pre-wetting liquid. Examples of a pre-wetting liquid include at least one of cyclopentanone (CyPe), cyclohexanone (CyH), monomethyl ether, propylene glycol monomethyl ether (PGME), propylene glycol monoethyl ether (PGEE), propylene glycol monomethyl ether acetate (PGMEA), propylene glycol monopropyl ether (PGPE), and ethyl lactate (EL). In some embodiments, the solvent can be a developer solution such as n-butyl acetate, or a rinsing liquid such as 4-methyl-2-pentanol (MIBC). In some embodiments, the solvent can be a rinse solvent used in a wafer manufacturing process, such as isopropyl alcohol.

In some embodiments, the pre-processed or unpurified organic solvent can have a purity of at most about 99% (e.g., at most about 98%, at most about 97%, at most about 96%, or at most about 95%). In some embodiments, the post-processed or purified organic solvent obtained from the methods described herein can have a purity of at least about 99.5% (e.g., at least about 99.9%, at least about 99.95%, at least about 99.99%, at least about 99.995%, at least about 99.999%, at least about 99.9995%, at least about 99.9999%, or 100%). As mentioned herein, "purity" refers to the weight percentage of the solvent in the total weight of the liquid. The content of the organic solvent in a liquid can be measured by using a gas chromatography mass spectrometry (GC-MS) device (e.g., a thermal desorption (TD) GC-MS device).

In some embodiments, the boiling point of the solvent described herein is at most about 200° C. (e.g., at most about 150° C.) or at least about 50° C. (e.g., at least about 100° C.) from a point of improving manufacturing yield of a semiconductor chip. For example, when the solvent is isopropanol, its boiling point is about 82.5° C. In this disclosure, the boiling point means a boiling point measured at 1 atm.

In general, impurities contained in a pre-processed organic solvent can include metallic impurities, particles, and others such as organic impurities and moisture.

As described herein, metal impurities can be in a form of a solid (e.g., metal simplex, particulate metal-containing compound, and the like). In some embodiments, metal impurities can include a metal selected from the group consisting of alkali metals, alkaline earth metals, main group metals, transition metals, and lanthanide metals. Examples of common metallic impurities include heavy metals such as copper (Cu), iron (Fe), aluminum (Al), chromium (Cr), lead (Pb), nickel (Ni), zinc (Zn), and lead (Pb); and alkali or alkaline earth metals such as sodium (Na), potassium (K), and calcium (Ca). Depending on the type of metal, metal impurities can deteriorate oxide integrity, degrade MOS gate stacks, and reduce lifetime of devices. In some embodiments, the content of each metal component in the pre-processed solvent ranges from about 0.1 to about 1000 ppt (e.g., from about 200 to about 1000 ppt or from about 500 to about 1000 ppt).

In an organic solvent purified by the methods described herein, the total trace metal content is preferred to be within a predetermined range of from 0 (e.g., at least about 1 ppt, at least about 5 ppt, or at least about 10 ppt) to at most about 200 ppt (e.g., at most about 180 ppt, at most about 160 ppt, at most about 150 ppt, at most about 140 ppt, at most about 120 ppt, at most about 100 ppt, at most about 50 ppt, or at most about 20 ppt) in mass, and the amount of each trace metal (e.g., Fe, Ni, Cr, Zn, Cu, K, Na, or Ca) is preferred to be within a predetermined range of from 0 (e.g., at least about 1 ppt, at least about 2 ppt, or at least about 3 ppt) to at most about 50 ppt (e.g., at most about 40 ppt, at most about 30 ppt, at most about 20 ppt, at most about 15 ppt, at most about 10 ppt, at most about 8 ppt, at most about 6 ppt, at most about 5 ppt, at most about 4 ppt, at most about 3 ppt, or at most about 2 ppt) in mass.

In the present disclosure, substances having a size of 0.03 µm or greater are referred to as "particles" or "particulates". Examples of particles include dust, dirt, organic solid matters, and inorganic solid matters. The particles can also include impurities of colloidalized metal atoms. The type of the metal atoms that are easily colloidalized is not particularly limited, and can include at least one metal atom selected from the group consisting of Na, K, Ca, Fe, Cu, Mg, Mn, Li, Al, Cr, Ni, Zn, and Pb. In an organic solvent purified by the methods described herein, the total number of the particles having a size of 0.03 µm or more (e.g., 0.05 µm or more) is preferred to be within a predetermined range of at most 100 (e.g., at most 80, at most 60, at most 50, at most 40, at most 20, at most about 10, at most about 5, at most about 1, or 0) per 1 ml of the solvent. The number of "particles" in a liquid medium can be counted by a light scattering type in-liquid particle counter and is referred as LPC (liquid particle count).

As described herein, organic impurities are different from the organic solvent and refer to organic matters that are contained in the content of 5000 mass ppm or smaller with respect to the total mass of the liquid containing the organic solvent and the organic impurities. Organic impurities can be volatile organic compounds that are present in ambient air even inside a clean-room. Some of the organic impurities originate from shipping and storage equipment, while some are presented in a raw material from the start. Other examples of organic impurities include a by-product generated when the organic solvent is synthesized and/or an unreacted reactant. Examples of organic impurities include aliphatic hydrocarbons (e.g., $C_8$-$C_{24}$ alkanes or alkenes having 8 or more carbons), aromatic hydrocarbons, ethers, esters, and aldehydes.

The total content of the organic impurities in a purified organic solvent is not particularly limited. From a point of improving the manufacturing yield of a semiconductor device, the total content of the organic impurities can be at most about 1000 ppb (e.g., at most about 500 ppb, at most about 400 ppb, at most about 300 ppb, at most about 200 ppb, at most about 100 ppb, at most about 50 ppb, at most about 20 ppb, at most about 10 ppb) and/or at least about 0.1 ppb (at least about 0.5 ppb or at least about 1 ppb) of the purified organic solvent. In some embodiments, the organic solvent is free of any organic impurities. The content of the organic impurities in the solvent described herein can be measured by using a gas chromatography mass spectrometry (GC-MS) device (e.g., a thermal desorption (TD) GC-MS device).

In some embodiments, the total amount of the moisture or water content can be at most about 100 ppm (e.g., at most about 50 ppm, at most about 40 ppm, at most about 30 ppm, at most about 20 ppm, at most about 10 ppm, at most about 5 ppm, at most about 2 ppm, at most about 1 ppm, at most about 500 ppb, at most about 100 ppb, or at most about 10 ppb) and/or at least about 1 ppb (e.g., at least about 1 ppm or at least about 20 ppm) of the purified organic solvent. In some embodiments, the purified organic solvent is free of water. The moisture or water content in the solvent described herein can be measured by using a gas chromatography mass spectrometry (GC-MS) device.

FIG. 1 is a schematic diagram showing a configuration of a purification system according to some embodiments of the present disclosure. As shown in FIG. 1, the purification system 10 includes supply unit 110, dehydration columns 112a and 112b, first filter unit 114, distillation column 120, storage tank 130, second filter unit 122, third filter unit 124, fourth filter unit 126, and packaging station 140, all of which are in fluid communication with each other (e.g., through one or more pipes or conduits). Purification system 10 also includes an optional first recirculation loop 150 connecting supply unit 110, dehydration columns 112a and 112b, and first filter unit 114, and an optional second recirculation loop 160 connecting storage tank 130, second filter unit 122, third filter unit 124, and fourth filter unit 126. In general, purification system 10 can include other components (such as pumps, temperature control units, supply ports, outflow ports, or valves) that are not shown in FIG. 1.

In general, supply unit 110 is configured to hold or transport a starting material (e.g., a pre-processed or unpurified organic solvent). The starting material can be processed by purification system 10 to produce or manufacture a purified organic solvent in which the number of unwanted contaminants (e.g., particulates, organic impurities, metallic impurities, and moisture) are limited within predetermined ranges. The type of supply unit 110 is not particularly limited as long as it continuously or intermittently supplies the starting material to the other components of purification system 10. In some embodiments, supply unit 110 can be a tank, such as a stationary tank or a mobile tank. In some embodiments, supply unit 110 can include a material receiving tank, a sensor such as a level gauge (not shown), a pump (not shown), and/or a valve (not shown) for controlling the flow of the starting material (not shown). In FIG. 1, purification system 10 includes one supply unit 110. However, in some embodiments, a plurality of supply units 110 can be provided (e.g., in parallel or series) for each type of starting materials to be processed by purification system 10.

Purification system 10 can include at least one pre-distillation filtration system 20 and at least one post-distillation filtration system 30. In general, pre-distillation filtration system 20 performs an initial filtration of the starting material (e.g., unpurified organic solvent) to remove moisture and/or large particles before distillation, and post-distillation filtration system 30 performs a filtration after distillation to remove any remaining impurities (e.g., metal or organic impurities) and fine particles to obtain a ultra-high purity organic solvent. In some embodiments, each of pre-distillation filtration system 20 and post-distillation filtration system 30 can include one or more filter units (each of which can include a filter housing and one or more filters (e.g., 1-20 filters)) in the filter housing, and certain other vessels (e.g., a storage tank) and impurity-removal columns (such as a dehydration column). For example, pre-distillation filtration system 20 shown in FIG. 1 includes supply unit 110, dehydration columns 112a/112b, and first filter unit 114, and post-distillation filtration system 30 shown in FIG. 1 includes storage tank 130, second filter unit 122, third filter unit 124, and fourth filter unit 126. Distillation column 120 shown in FIG. 1 is generally used to remove the majority of the organic and metal impurities and particles.

In some embodiments, purification system 10 can optionally include one or more temperature control units (not shown in FIG. 1) for setting or maintaining the temperature of the organic solvent within a certain temperature range such that the organic solvent is maintained at a substantially consistent temperature during certain part of the purification process. As described herein, a temperature control unit can include, but are not limited to, a commercial re-circulating heating/cooling unit, a condenser, or a heat exchanger, which can be installed, for example, on distillation column 120 or on a conduit at any suitable location in purification system 10.

In some embodiments, an organic solvent can be purified by purification system 10 at ambient temperature. In such embodiments, purification system 10 may not need a temperature control unit except for those that may be needed for distillation column 120.

In some embodiments, purification system 10 can include at least one (e.g., two or three) column containing an adsorbent (e.g., dehydration columns) to remove moisture or certain other impurities in the unpurified organic solvent. In some embodiments, the adsorbent in such a column can include a molecular sieve (e.g., zeolite 3A, zeolite 4A, or zeolite 5A), a silica gel, activated alumina, activated carbon or an ion exchange resin. In some embodiments, when one column containing an adsorbent is not sufficient to lower moisture in the organic solvent to a desired level (e.g., at most about 100 ppm), two or more of such columns can be used. For example, FIG. 1 shows that two dehydration columns 112*a* and 112*b* are used in purification system 10. In such embodiments, dehydration columns 112*a* and 112*b* can be in fluid communication with each other and are connected in series.

In some embodiments, each filter unit in purification system 10 can include a filter housing and one or more (e.g., 2, 3, 4, or 5) filters in the filter housing. Each filter can include a filtration medium made from a suitable material and having an appropriate average pore size. The filters can be arranged in parallel or in series in the filter housing. During use, when two filters are arranged in parallel, a solvent to be purified passes these two filters in parallel (i.e., substantially at the same time). On the other hand, when two filters are arranged in series, a solvent to be purified passes these two filters sequentially during use. In some embodiments, some filter units can include a plurality of filters in parallel in the filter housing to increase flow rate and improve productivity.

For example, purification system 10 shown in FIG. 1 includes four filter units (i.e., units 114, 122, 124, and 126), each of which includes a filter housing and one or more filters in the filter housing. In other embodiments, purification system 10 can also include other purification modules in addition to the four filter units shown in FIG. 1.

Referring to FIG. 1, filter units 114, 122, 124, and 126 can be different in functionality or property and offer different purification treatments. In some embodiments, each filter unit can independently be selected from the group consisting of a particle removal filter, an ion exchange filter, and an ion absorption filter. In some embodiments, the filters accommodated within each of filter units 114, 122, 124, and 126 can have the same or similar purification function, physiochemical properties, pore size and/or construction material.

In some embodiments, purification system 10 can include at least one (e.g., two or three) first filter unit 114 between dehydration column 112*b* and distillation column 120 and in fluid communication with columns 112*b* and 120. First filter unit 114 can include a filter housing and at least one (e.g., 2, 3, 4, or 5) filter in the filter housing. In some embodiments, when first filter unit 114 includes two or more filters, these filters can be arranged in parallel to improve flow rate and productivity.

In some embodiments, the filters in first filter unit 114 can be a particle removal filter to remove relatively large particles from the organic solvent. In some embodiments, the filters in first filter unit 114 can include a filtration medium having an average pore size of at most about 0.25 μm or 250 nm (e.g., at most about 240 nm, at most about 220 nm, at most about 200 nm, at most about 180 nm, at most about 160 nm, or at most about 150 nm) and/or at least about 0.1 μm or 100 nm (e.g., at least about 110 nm, at least about 120 nm, at least about 130 nm, at least about 140 nm, or at least about 150 nm). Within the above range, it is possible to reliably remove foreign matters such as impurities or aggregates contained in the organic solvent while suppressing clogging of the filters in first filter unit 114.

Examples of suitable materials of the filtration media in the filters in first filter unit 114 include a fluoropolymer (e.g., polytetrafluoroethylene (PTFE), perfluoroalkoxy alkane polymers (PFA), or a modified polytetrafluoroethylene (MPTFE)), a polyamide such as nylon (e.g., nylon 6 or nylon 66), a polyolefin (including high density and ultrahigh molecular weight resins) such as polyethylene (PE) and polypropylene (PP), or a copolymer thereof. For example, the filtration medium in a particle removal filter can be made of at least one polymer selected from the group consisting of polypropylene (e.g., high density polypropylene), polyethylene (e.g., high density polyethylene (HDPE), or ultra high molecular weight polyethylene (UPE)), nylon, polytetrafluoroethylene, or a perfluoroalkoxy alkane polymer. A filter made of the above materials can effectively remove foreign matters (e.g., those having high polarity) which are likely to cause residue defects and/or particle defects, and to efficiently reduce the content of the metal components in the organic solvent.

In some embodiments, at least some (e.g., all) of the filters can be arranged in first filter unit 114 in parallel and the remaining filters in first filter unit 114 (if any) can be arranged in series. In some embodiments, first filter unit 114 can include two or three filters that are arranged in parallel, have an average pore size of about 100 nm, and include a filtration medium made from polytetrafluoroethylene.

Without wishing to be bound by theory, it is believed that using a combination of dehydration column and first filter unit in purification system 10 can significantly lower the moisture content of the purified organic solvent without increasing the amounts of particles and other impurities in the purified organic solvent. For example, when using a combination of dehydration column and first filter unit in purification system 10, the purified organic solvent can have a moisture content of at most about 100 ppm (to at least about 1 ppm. Further, without wishing to be bound by theory, it is believed that a dehydration column may release contaminants (e.g., particles) during use and using first filter unit 114 can significantly lower the amount of such contaminants in the purified organic solvent.

During the purification process, if the purity level of the organic solvent exiting first filter unit 114 meets the predetermined requirements (e.g., having a moisture content of at most about 100 ppm), the organic solvent can be transferred to distillation column 120 for distillation. On the other hand, if the purity level of the organic solvent exiting first filter unit 114 does not meet the predetermined requirements, the organic solvent can be transferred back to supply unit 110 through optional first recirculation loop 150 and be purified again by dehydration columns 112*a*/112*b* and first filter unit 114.

In some embodiments, purification system 10 includes at least one (e.g., two or three) distillation column 120 between pre-filtration system 20 and post-distillation system 30. As shown in FIG. 1, distillation column 120 is disposed between first filter unit 114 and storage 130 and is in fluid communication with unit 114 and tank 130. In general, distillation column 120 can be any suitable distillation column known in the art and is used to purify the organic solvent through distillation to remove the majority of the organic and metal impurities and particles.

In some embodiments, purification system 10 includes at least one (e.g., two or three) storage tank 130 between distillation column 120 and second filter unit 122 and is in fluid communication with column 120 and unit 122. In general, storage tank 130 can be any suitable storage tank known in the art and can be used to store the organic solvent. In some embodiments, storage tank 130 can be filled with nitrogen to minimize the moisture and oxidation of the solvent stored in the tank. During the purification process, the organic solvent exiting distillation column 120 can be first transferred to storage tank 130, and then can pass through filter units 122, 124, and 126 to remove impurities. If the purity level of the organic solvent exiting filter unit 126 meets the predetermined requirements (e.g., having a purity of at least about 99.99%, a moisture content of at most about 100 ppm, and/or metal impurities in a total amount of at most about 200 ppt), the organic solvent can be transferred to package station 140. On the other hand, if the purity level of the purified organic solvent does not meet the predetermined requirements, the organic solvent can then be transferred back to storage tank 130 through optional second recirculation loop 160 and be purified again by filter units 122, 124, and 126.

In general, storage tank 130 can be any suitable vessel for storing a chemical liquid. In some embodiments, storage tank 130 can have a suitable volume. For example, storage tank 130 can have a volume of at least about 1000 liters (e.g., at least about 2000 liters, at least about 3000 liters, or at least about 5000 liters) and/or at most about 30,000 liters (e.g., at most about 25,000 liters, at most about 20,000 liters, at most about 15,000 liters, or at most about 10,000 liters).

In some embodiments, purification system 10 can include at least one (e.g., two or three) second filter unit 122 between storage tank 130 and third filter unit 124 and in fluid communication with tank 130 and unit 124. In some embodiments, second filter unit 122 can include a filter housing and at least one (e.g., 2, 3, 4, or 5) filters in the filter housing. The filters in second filter unit 122 can be a particle removal filter to remove relative small particles from the organic solvent. In some embodiments, the filters in second filter unit 122 can include a filtration medium having an average pore size of at most about 50 nm (e.g., at most about 45 nm, at most about 40 nm, at most about 35 nm, at most about 30 nm, at most about 25 nm, or at most about 20 nm) and/or at least about 5 nm (e.g., at least about 10 nm, at least about 15 nm, at least about 20 nm, at least about 25 nm, or at least about 30 nm). In some embodiments, the average pore size of the filtration medium in the filters in second filter unit 122 can be smaller than the average pore size of the filtration medium in the filters in first filter unit 114. In such embodiments, second filter unit 122 can be used to remove particles smaller than those removed by first filter unit 114.

Examples of suitable materials of the filtration media in the filters in second filter unit 122 include a fluoropolymer (e.g., polytetrafluoroethylene (PTFE), perfluoroalkoxy alkane polymers (PFA), or a modified polytetrafluoroethylene (MPTFE)), a polyamide such as nylon (e.g., nylon 6 or nylon 66), a polyolefin (including high density and ultrahigh molecular weight resins) such as polyethylene (PE) and polypropylene (PP), or a copolymer thereof. For example, the filtration medium in a particle removal filter can be made of at least one polymer selected from the group consisting of polypropylene (e.g., high density polypropylene), polyethylene (e.g., high density polyethylene (HDPE), or ultra high molecular weight polyethylene (UPE)), nylon, polytetrafluoroethylene, or a perfluoroalkoxy alkane polymer.

In some embodiments, at least some (e.g., all) of the filters can be arranged in second filter unit 122 in parallel and the remaining filters in second filter unit 122 (if any) can be arranged in series. In some embodiments, second filter unit 122 can include two or three filters that are arranged in parallel, have an average pore size of about 50 nm, and include a filtration medium made from polytetrafluoroethylene.

In some embodiments, purification system 10 can include at least one (e.g., two or three) third filter unit 124. In some embodiments, third filter unit 124 can be an ion exchange filter unit that includes at least one (e.g., 2, 3, 4, or 5) first ion exchange filter and at least one (e.g., 2, 3, 4, or 5) second ion exchange filter in the housing. In some embodiments, the at least one first ion exchange filter and the at least one second ion exchange filter are both negatively charged ion exchange filters or cationic ion exchange filters (i.e., including one or more filtration medium containing a negatively charged ion exchange resin) and are connected in series. When there are more than one first ion exchange filter, the multiple first ion exchange filters can be connected in parallel to increase flow rate and productivity. When there are more than one second ion exchange filter, the multiple second ion exchange filters can be connected in parallel to increase flow rate and productivity.

In general, the at least one first ion exchange filter is different from the at least one second ion exchange filter (e.g., containing different filtration media). In some embodiments, the at least one first ion exchange filter can be capable of primarily removing heavy metals (e.g., Fe, Ni, Cr, Zn, or Cu), while the at least one second ion exchange filter can be capable of primarily removing alkali or alkaline earth metals (e.g., K, Na, or Ca). In some embodiments, the first ion exchange filter can be capable of removing at least about 90 wt % (e.g., at least about 92 wt % or at least about 95 wt %) of one or more heavy metals and/or at most about 10 wt % (e.g., at most about 8 wt % or at most about 5 wt %) of one or more alkali or alkaline earth metals in the organic solvent. In some embodiments, the second ion exchange filter can be capable of removing at least about 70 wt % (e.g., at least about 75 wt %, at least about 80 wt %, at least about 85 wt %, or at least about 90 wt %) one or more alkali or alkaline earth metals and/or at most about 30 wt % (e.g., at most about 25 wt %, at most about 20 wt %, at most about 15 wt %, or at most about 10 wt %) one or more heavy metals in the organic solvent.

In some embodiments, it is preferable that the at least one second ion exchange filter is disposed downstream of the at least one first ion exchange filter. Without wishing to be bound by theory, it is believed that, in such embodiments, heavy metals in the organic solvent can be removed first, which facilitates the removal of alkali or alkaline earth metals because residual heavy metals in the organic solvent may impede the removal of alkali or alkaline earth metals by the at least one second ion exchange filter. In some embodiments, the sequence of the at least one first and second ion exchange filters in third filter unit 124 can be reversed.

In some embodiments, the at least one first or second ion exchange filters in filter unit 124 can include one or more negatively charged ion exchange resin membranes as a filtration medium to remove positively charged particles and/or cationic metal ions from the organic solvent. The negatively charged ion-exchange resin membrane used in the present disclosure is not particularly limited, and filters including an ion exchange resin having a suitable ion-exchange group immobilized to a resin membrane can be used. Examples of such ion-exchange resin membranes include strongly acidic cation-exchange resins having a cation-exchange group (such as a sulfonic acid or sulfonate group) chemically modified on the resin membrane. Examples of suitable resin membranes include those containing cellulose, diatomaceous earth, a polyamide (e.g., nylon), a polyolefin (such as polyethylene (e.g., high density polyethylene or ultra high molecular weight polyethylene), polypropylene, or polystyrene), a resin having an imide group, a resin having an amide group and an imide group, a fluoropolymer (e.g., a polytetrafluoroethylene or a perfluoroalkoxy alkane polymer), or a copolymer or combination thereof. In some embodiments, the ion-exchange resin membrane can be a membrane having an integral structure of a particle-removing membrane and an ion-exchange resin membrane. Polyalkylene (e.g., PE, PP, or PTFE) membranes with a cation-exchange group (e.g., a sulfonate group) chemically modified thereon are preferred. Filters with cation-exchange resin membranes used in the present disclosure can be commercially available filters with metal ion removal functionality. Commercial example of such a cation-exchange filter include IonKleen filters available from Pall Corporation (Port Washington, NY) and Protego Plus filters available from Entegris (Billerica, MA). These filters can be selected based on the ion exchange efficiency and have an estimated pore size in the range of about 100 nm to about 500 nm.

Examples of the shape of the membrane material in the at least one first or second ion exchange filters in filter unit 124 include a pleated type, a flat membrane type, a hollow fiber type, a porous body as described in JP-A No. 2003-112060 and the like. In some embodiments, when the ion exchange membrane has porosity, it is also possible to remove at least a portion of the fine particles in the organic solvent.

In some embodiments, the at least one first ion exchange filter in filter unit 124 can include a filtration medium that includes a polyethylene having sulfonate groups, a polytetrafluoroethylene having sulfonate groups, or a copolymer thereof, which is capable of primarily removing heavy metals (e.g., Fe, Ni, Cr, Zn, or Cu). A commercial example of such a filter is an IonKleen filter (such as IonKleen SL filters) from Pall Corporation (Port Washington, NY). In some embodiments, filter unit 124 can include two or three such first ion exchange filters connected in parallel to increase productivity.

In some embodiments, the at least one second ion exchange filter in filter unit 124 can include a filtration medium that includes a polyethylene having sulfonate groups, a polytetrafluoroethylene having sulfonate groups, or a copolymer thereof, which is capable of primarily removing alkali or alkaline earth metals (e.g., K, Na, or Ca). Commercial examples of such a filter include Protego Plus filters (such as Protego Plus IPA filters) and Protego AT 5 nm/Ionex combo filters available from Entegris (Billerica, MA). In some embodiments, third filter unit 124 can include two or three such second ion exchange filters connected in parallel to increase productivity.

Without wishing to be bound by theory, the inventors surprisingly found that including two different types of ion exchange filters in third filter unit 124 can significantly reduce the amount of metal impurities (e.g., to a total amount of at most about 200 ppt) in the purified organic solvent, compared to a system in which only one type of ion exchange filter is used.

In some embodiments, purification system 10 can include at least one (e.g., two or three) fourth filter unit 126 between third filter unit 124 and packaging station 140 (i.e., downstream of unit 124), and in fluid communication with unit 124 and station 140. In some embodiments, fourth filter unit 126 can include a filter housing and at least one (e.g., 2, 3, 4, or 5) filters in the filter housing. The filters in fourth filter unit 126 can be a particle removal filter to remove relative small particles from the organic solvent. In some embodiments, the filters in fourth filter unit 126 can include a filtration medium having an average pore size of at most about 10 nm (e.g., at most about 9 nm, at most about 8 nm, at most about 7 nm, at most about 6 nm, at most about 5 nm, or at most about 4 nm) and/or at least about 2 nm (e.g., at least about 3 nm, at least about 4 nm, or at least about 5 nm). In some embodiments, the average pore size of the filtration medium in the filters in fourth filter unit 126 can be smaller than the average pore size of the filtration medium in the filters in second filter unit 122. In such embodiments, fourth filter unit 126 can be used to remove particles smaller than those removed by second filter unit 122.

Examples of suitable materials of the filtration media in the filters in fourth filter unit 126 include a fluoropolymer (e.g., polytetrafluoroethylene (PTFE), perfluoroalkoxy alkane polymers (PFA), or a modified polytetrafluoroethylene (MPTFE)), a polyamide such as nylon (e.g., nylon 6 or nylon 66), a polyolefin (including high density and ultrahigh molecular weight resins) such as polyethylene (PE) and polypropylene (PP), or a copolymer thereof. For example, the filtration medium in a particle removal filter can be made of at least one polymer selected from the group consisting of polypropylene (e.g., high density polypropylene), polyethylene (e.g., high density polyethylene (HDPE), or ultra high molecular weight polyethylene (UPE)), nylon, polytetrafluoroethylene, or a perfluoroalkoxy alkane polymer. A filter made of the above material can effectively remove foreign matters (e.g., those having high polarity) which are likely to cause residue defects and/or particle defects, and to efficiently reduce the content of the metal components in the organic solvent.

In some embodiments, at least some (e.g., all) of the filters can be arranged in fourth filter unit 126 in parallel and the remaining filters in fourth filter unit 126 (if any) can be arranged in series. In some embodiments, fourth filter unit 126 can include two or three filters that are arranged in parallel, have an average pore size of about 10 nm, and include a filtration medium made from polytetrafluoroethylene.

In some embodiments, purification system 10 can optionally include a recirculation conduit to form first recirculation loop 150 for recirculating a partially-purified organic solvent back to supply unit 110, which can be purified by dehydration columns 112a/112b and first filter unit 114 again. In some embodiments, purification system 10 can optionally include a recirculation conduit to form second recirculation loop 160 for recirculating a partially-purified organic solvent back to storage tank 130, which can be purified by filter units 122, 124, and 126 again. In some embodiments, the partially-purified organic solvent is recirculated through first recirculation loop 150 or second recirculation loop 160 at least two times (e.g., at least three times, at least four times, or at least five times) before the organic solvent is transferred to packaging station 140.

In some embodiments, filter units 114, 122, 124, and 126 in purification system 110 may not include filter housings, and the filters in filter units 114, 122, 124, and 126 can be configured un-compartmentalized in purification system 10.

For example, purification system 10 can be a multistage system including replaceable filters (e.g., those in filter units 114, 122, 124, and 126) that are concatenated together inside purification system 10, and the organic solvent can be caused to cascade through these filters.

In some embodiments, packaging station 140 can be a mobile storage tank (e.g., a tank on a tanker) or a fixed storage tank. In some embodiments, packaging station 140 can be a fluoropolymer lined equipment (e.g., the inner surface of which can include a fluoropolymer such as a PTFE). In some embodiments, packaging station 140 can have a volume of at least about 100 liters (e.g., at least about 200 liters, at least about 300 liters, or at least about 500 liters) and/or at most about 1,500 liters (e.g., at most about 1200 liters, at most about 1000 liters, at most about 900 liters, at most about 800 liters, at most about 700 liters, or at most about 600 liters).

The present disclosure also features methods of purifying a solvent (e.g., an organic solvent such as isopropyl alcohol). In some embodiments, the purification method can include (1) passing the organic solvent through at least one column containing an adsorbent (e.g., dehydration columns 112a/112b shown in FIG. 1) to remove residual moisture in the organic solvent, (2) passing the organic solvent through a first filter unit (e.g., first filter unit 114 shown in FIG. 1), in which the first filter unit includes a first housing and at least one filter in the first housing, and the at least one filter includes a filtration medium; and (3) distilling the organic solvent in a distillation column (e.g., distillation column 120 shown in FIG. 1) to obtain a purified organic solvent.

In some embodiments, the purification method can include (1) distilling the organic solvent in a distillation column to obtain a distilled organic solvent; and (2) passing the distilled organic solvent through an ion exchange filter unit (e.g., third filter unit 124 shown in FIG. 1) to obtain a purified organic solvent, in which the ion exchange filter unit includes a housing, and at least one first ion exchange filter and at least one second ion exchange filter in the housing; the at least one first ion exchange filter and the at least one second ion exchange filter are both negatively charged ion exchange filters and are connected in series; and the at least one first ion exchange filter is different from the at least one second ion exchange filter.

For example, referring to FIG. 1, an unpurified or pre-processed solvent (i.e., a starting material) can be purified by purification system 10 by passing the solvent from supply unit 110 through dehydration columns 112a/112b and first filter units 114 to distillation column 120, distilling the solvent in distillation column 120, transferring the solvent exiting distillation column 120 to storage tank 130, and passing the solvent from storage tank 130 through filter units 122, 124, and 126 to packaging station 140.

In some embodiments, the purification methods described herein can include recirculating the solvent through recirculation loop 150 in pre-distillation filtration system 20 (e.g., through supply unit 110, dehydration columns 112a/112b, and first filter unit 114) at least one time (e.g., two or three times) before transferring the partially-purified solvent to distillation column 120. For example, the recirculating can include moving the organic solvent exiting first filter unit 114 to supply unit 110 and subsequently passing the organic solvent through dehydration columns 112a/112b (which include an adsorbent) and first filter unit 114 one or more times until the moisture level in the organic solvent is within a predetermined range.

In some embodiments, the purification methods described herein can include recirculating the solvent through recirculation loop 160 in post-distillation filtration system 30 (e.g., through filter units 122, 124, and 126, and storage tank 130) at least one time (e.g., two or three times) before transferring the purified solvent to packaging station 140. For example, the recirculating can include moving the organic solvent exiting fourth filter unit 126 to storage tank 130 and subsequently passing the organic solvent through second filter unit 122, third filter unit 124 (which can be an ion exchange filter unit that includes two different types of ion exchange filters), and fourth filter unit 126 one or more times until the purity and the total amount of trace metals in the organic solvent are within predetermined ranges.

When the number of particles and the amount of impurities detected from the purified solvent at the end of the purification process are controlled within predetermined ranges, an ultra-high purity solvent (e.g., having a purity of at least about 99.99%, a moisture content of at most about 100 ppm, and/or metal impurities in a total amount of at most about 200 ppt) is produced. Subsequently, the ultra-high purity solvent can be transferred to either packaging station 140 for storage or to a manufacturing process for making a semiconductor article.

In some embodiments, the solvent purified by the methods and systems described herein can form a film or coating having an on-wafer particle count of at most about 500 (e.g., at most about 450, at most about 400, at most about 350, at most about 300, at most about 250, at most about 200, at most about 150, at most about 100, at most about 50 or at most about 25) or 0 on an entire wafer (e.g., a 12-inch wafer). In some embodiments, the solvent purified by the methods and systems described herein can form a film or coating having an on-wafer metal count (e.g., either a total on-wafer metal count or an on-wafer metal count of a specific metal such as Fe or Ni) of at most about 100 (e.g., at most about 90, at most about 80, at most about 70, at most about 60, at most about 50, at most about 40, at most about 30, at most about 20, or at most about 10) or 0 on an entire wafer (e.g., a 12-inch wafer). In some embodiments, the solvent purified by the methods and systems described herein can form a film or coating having an defect density (i.e., based on the total count of on-wafer metal and particles) of at most about 1.5 (e.g., at most about 1.4, at most about 1.2, at most about 1, at most about 0.8, at most about 0.6, at most about 0.5, at most about 0.4, at most about 0.2, at most about 0.1, at most about 0.07, at most about 0.05, at most about 0.03, at most about 0.02, at most about 0.01, at most about 0.007, at most about 0.005, at most about 0.004, at most about 0.003) or 0 per square centimeter on an entire wafer (e.g., a 12-inch wafer).

In some embodiments, the solvent can be purified by the methods and systems described herein at a relatively high flow rate. For example, the solvent can be purified at a flow rate of at least about 1 L/min (e.g., at least about 2 L/min, at least about 4 L/min, at least about 5 L/min, at least about 6 L/min, at least about 8 L/min, at least about 10 L/min, or at least about 15 L/min) and/or at most about 50 L/min (e.g., at most about 45 L/min, at most about 40 L/min, at most about 35 L/min, at most about 30 L/min, at most about 25 L/min, at most about 20 L/min, or at most about 15 L/min) through purification system 10. In general, the flow rate for purifying a solvent can vary depending on a number of factors, including the nature and viscosity of the solvent to be purified, the temperature, the number of the filters (e.g., those arranged in parallel), the type and number of other equipment used in the purification process. Without wishing to be bound by theory, it is believed that the flow rate of the solvent to be purified cannot be too high to minimize defects on a wafer and to minimize buildup of static electric charges in the inner surface of a conduit or vessel, which can erode the conduit or vessel.

The present disclosure is illustrated in more detail with reference to the following examples, which are for illustrative purposes and should not be construed as limiting the scope of the present disclosure.

EXAMPLES

General Description of Trace Metal Measurement

The total trace metal concentration in a solvent sample was tested using ICP-MS (inductively coupled plasma mass spectrometry (ICP-MS). Using a Fujifilm developed method, each sample was tested for the presence of 36 metal species, the detection limit was metal specific, but the typical detection limits were in the range of 0.00010-0.030 ppb.

General Description of Trace Moisture and Organic Impurities Measurement

The trace moisture and organic impurities in a liquid sample are measured by Thermal Desorption-Gas Chromatography/Mass Spectrometry (TD-GC/MS). A small volume of a liquid sample is injected into a thermal desorption tube containing a sorbent, and put into a thermal desorber. The sample is heated, then injected into the GC/MS unit where the sample mixture is separated into its components and components are identified by mass.

Example 1

Isopropyl alcohol (IPA) was purified in the purification system shown in FIG. 1. The test results are summarized in Table 1 below.

TABLE 1

| Contaminants | Before Purification | After Purification |
|---|---|---|
| Purity (%) | 99.99 | >99.99 |
| Water (ppm) | 400 | 40 |
| n-Propanol (ppm) | 405.2 | 7 |
| Acetone (ppm) | 170.8 | 8.8 |
| Total Organics + C6 (ppb) | 1127.81 | 349.88 |
| Al (ppb) | 1 | 0.005 |
| As (ppb) | 8.9 | 0.008 |
| Sb (ppb) | 1 | 0.004 |
| Ba (ppb) | 1 | 0.002 |
| Be (ppb) | 1 | 0.008 |
| Bi (ppb) | 1 | 0.004 |
| B (ppb) | 1 | 0.037 |
| Cd (ppb) | 1 | 0.004 |
| Ca (ppb) | 1 | 0.02 |
| Cr (ppb) | 1.6 | 0.005 |
| Co (ppb) | 1 | 0.004 |
| Cu (ppb) | 1 | 0.004 |
| Ga (ppb) | 1 | 0.004 |
| Ge (ppb) | 1 | 0.004 |
| Au (ppb) | 1 | 0.002 |
| In (ppb) | 1 | 0.004 |
| Fe (ppb) | 5.8 | 0.009 |
| Pb (ppb) | 1 | 0.003 |
| Li (ppb) | 1 | 0.005 |
| Mg (ppb) | 1 | 0.004 |
| Mn (ppb) | 1 | 0.004 |
| Mo (ppb) | 1 | 0.003 |
| Ni (ppb) | 1 | 0.005 |
| Nb (ppb) | 1 | 0.004 |
| K (ppb) | 1.9 | 0.004 |
| Ru (ppb) | 1 | 0.004 |
| Ag (ppb) | 1 | 0.004 |
| Na (ppb) | 3.6 | 0.005 |
| Sr (ppb) | 1 | 0.003 |
| Ta (ppb) | 1 | 0.002 |
| Tl (ppb) | 1 | 0.004 |
| Sn (ppb) | 1 | 0.003 |
| Ti (ppb) | 1 | 0.004 |
| V (ppb) | 1 | 0.004 |
| Zn (ppb) | 14.3 | 0.009 |
| Zr (ppb) | 1 | 0.003 |

"Total Organics + C6" refers to the total amount of organic impurities having six carbons or more.

As shown in Table 1, the moisture content, amounts of organic impurities, and amounts of the trace metal in the isopropyl alcohol purified by purification system 10 were significantly reduced.

While the invention has been described in detail with reference to certain embodiments thereof, it will be understood that modifications and variations are within the spirit and scope of that which is described and claimed.

What is claimed is:

1. A method for removing impurities from an organic solvent, comprising:
    distilling the organic solvent in a distillation column to obtain a distilled organic solvent; and
    passing the distilled organic solvent through an ion exchange filter unit to obtain a purified organic solvent;
    wherein the ion exchange filter unit comprises at least one first ion exchange filter and at least one second ion exchange filter, the at least one first ion exchange filter and the at least one second ion exchange filter are both negatively charged ion exchange filters and are connected in series, the at least one first ion exchange filter comprises a filtration medium comprising a polyolefin or a copolymer thereof, the at least one second ion exchange filter comprises a filtration medium comprising a fluoropolymer or a copolymer thereof, and the at least one second ion exchange filter is disposed downstream of the at least one first ion exchange filter; and
    wherein the at least one first ion exchange filter is capable of removing at least 90 wt % of each of Fe, Ni, Cr, Zn, and Cu from the organic solvent.

2. The method of claim 1, wherein the organic solvent comprises an alcohol.

3. The method of claim 1, wherein the organic solvent comprises isopropyl alcohol.

4. The method of claim 1, wherein the filtration medium in the at least one first ion exchange filter comprises a polyethylene having sulfonate groups or a copolymer thereof.

5. The method of claim 1, wherein the ion exchange filter unit comprises two to five first ion exchange filters.

6. The method of claim 5, wherein the first ion exchange filters are connected in parallel.

7. The method of claim 1, wherein the filtration medium in the at least one second ion exchange filter comprises a polytetrafluoroethylene having sulfonate groups or a copolymer thereof.

8. The method of claim 1, wherein the ion exchange filter unit comprises two to five second ion exchange filters.

9. The method of claim 8, wherein the second ion exchange filters are connected in parallel.

10. The method of claim 1, wherein the at least one second ion exchange filter is capable of removing at least 70 wt % of K, Na, or Ca from the organic solvent.

11. The method of claim 1, further comprising passing the organic solvent through a filter unit in fluid communication with and between the distillation column and the ion exchange filter unit.

12. The method of claim 11, wherein the filter unit between the distillation column and the ion exchange filter unit comprises a housing and at least one particle removal filter in the housing.

13. The method of claim 12, wherein the at least one particle removal filter comprises a filtration medium that comprises a polyolefin, a polyamide, a fluoropolymer, or a copolymer thereof.

14. The method of claim 13, wherein the at least one particle removal filter comprises a filtration medium that comprises a polytetrafluoroethylene.

15. The method of claim 12, wherein the at least one particle removal filter comprises a filtration medium having an average pore size of from about 5 nm to about 50 nm.

16. The method of claim 1, further comprising passing the organic solvent through a filter unit downstream of and in fluid communication with the ion exchange filter unit.

17. The method of claim 16, wherein the filter unit downstream of the ion exchange filter unit comprises a housing and at least one particle removal filter in the housing.

18. The method of claim 17, wherein the at least one particle removal filter in the filter unit downstream of the ion exchange filter unit comprises a filtration medium that comprises a polyolefin, a polyamide, a fluoropolymer, or a copolymer thereof.

19. The method of claim 18, wherein the at least one particle removal filter in the filter unit downstream of the ion exchange filter unit comprises a filtration medium that comprises a polytetrafluoroethylene.

20. The method of claim 17, wherein the at least one particle removal filter in the filter unit downstream of the ion exchange filter unit comprises a filtration medium having an average pore size of from about 2 nm to about 10 nm.

21. The method of claim 16, further comprising recirculating the organic solvent exiting the filter unit downstream of the ion exchange filter unit.

22. The method of claim 21, wherein the recirculating comprises moving the organic solvent exiting the filter unit downstream of the ion exchange filter unit to a storage tank and subsequently passing the organic solvent through the ion exchange filter unit.

23. The method of claim 1, further comprising moving the purified solvent to a packaging station.

24. The method of claim 1, wherein the purified organic solvent comprises metal impurities in a total amount of at most about 200 ppt of the purified organic solvent.

25. The method of claim 1, wherein the ion exchange filter unit comprises a housing and the at least one first and second ion exchange filters are in the housing.

* * * * *